(12) United States Patent
Von Hebel et al.

(10) Patent No.: US 6,897,343 B2
(45) Date of Patent: May 24, 2005

(54) PROCESS FOR THE PREPARATION OF PROPANEDIOL

(75) Inventors: Klaas Lambertus Von Hebel, Amsterdam (NL); Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/742,361

(22) Filed: Dec. 19, 2003

(65) Prior Publication Data

US 2004/0152927 A1 Aug. 5, 2004

(30) Foreign Application Priority Data

Dec. 20, 2002 (EP) .............................................. 02258907

(51) Int. Cl.$^7$ ........................ C07C 29/48; C07C 29/16; C07C 29/15; C07C 29/00; C07C 29/132; C07C 27/041

(52) U.S. Cl. ...................... 568/867; 568/866; 568/908; 568/852; 558/277

(58) Field of Search ................................ 568/867, 908, 568/852, 866; 558/277

(56) References Cited

U.S. PATENT DOCUMENTS 4,508,927 A    4/1985   Bhise et al. ................ 568/858
5,847,189 A    12/1998  Tojo et al. .................. 558/277

FOREIGN PATENT DOCUMENTS

| EP | 776890 | 6/1997 |
|----|--------|--------|
| EP | 02256347.2 | 9/2002 |
| WO | WO 03/000641 | 1/2003 |
| WO | WO 03/042141 | 5/2003 |
| WO | WO 03/042152 | 5/2003 |

OTHER PUBLICATIONS

Buchanan et al. (U.S. Pre–Grant Pubs. 2003/0045739 A1).*

* cited by examiner

*Primary Examiner*—Elvis O. Price

(57) ABSTRACT

The invention relates to a process for the preparation of 1,2-propanediol from propylene oxide, which process involves contacting propylene oxide with carbon dioxide in the presence of a homogeneous phosphorus containing catalyst to obtain propylene carbonate, optionally removing at least part of the carbon dioxide, adding water and/or an alcohol to the reaction product containing propylene carbonate and phosphorus containing catalyst and contacting the mixture with a heterogeneous catalyst to obtain 1,2-propanediol in combination with dialkylcarbonate and/or carbon dioxide, and separating 1,2-propanediol from the reaction product obtained.

10 Claims, No Drawings

PROCESS FOR THE PREPARATION OF PROPANEDIOL

FIELD OF THE INVENTION

The present invention relates to a process for the preparation of propanediol from propylene oxide.

BACKGROUND OF THE INVENTION

Alkylene oxide may be converted into a cyclic alkylene carbonate in the presence of a suitable catalyst. Such processes have been described for example in U.S. Pat. No. 4,508,927 and Japanese patent application No. 73022702. These patent specifications describe processes in which an alkylene oxide is reacted with carbon dioxide in the presence of a catalyst containing phosphorus to form the cyclic alkylene carbonate. The catalyst can be an organic phosphonium halide as described in U.S. Pat. No. 4,508,927 or an organic trisubstituted phosphine as described in Japanese patent application No. 73022702.

WO-A-03/000641, which is a not-prepublished document, relates in its second aspect to the use of a homogeneous carbonation catalyst in a first carbonation reaction zone and a heterogeneous transesterification catalyst in a second reaction zone for reacting ethylene oxide with carbon dioxide. The carbonation catalysts preferably are alkali metal halides such KI or quaternary ammonium halides.

U.S. Pat. No. 5,847,189 describes processes for hydrolyzing cyclic alkylene carbonates to produce a diol and carbon dioxide. Additionally, U.S. Pat. No. 5,847,189 describes that it is advantageous to convert cyclic alkylene carbonate with an alcohol into alkylene glycol and a dialkylcarbonate.

SUMMARY OF THE INVENTION

The present invention provides a process for the preparation of 1,2-propanediol from propylene oxide, which process comprises:

(a) contacting propylene oxide with carbon dioxide in the presence of a homogeneous phosphorus containing catalyst to obtain propylene carbonate, (b) optionally removing at least part of the carbon dioxide, (c) adding water and/or an alcohol to the reaction product containing propylene carbonate and phosphorus containing catalyst and contacting the mixture with a heterogeneous catalyst to obtain 1,2-propanediol in combination with dialkylcarbonate and/or carbon dioxide, and (d) separating 1,2-propanediol from the reaction product obtained.

DETAILED DESCRIPTION OF THE INVENTION

The process according to the present invention allows the use of an active heterogeneous catalyst for the hydrolysis and/or transesterification of the propylene carbonate while still allowing a close integration of the conversion of the propylene oxide into propylene carbonate and the conversion of the propylene carbonate into 1,2-propanediol. Such integration is attractive in that it results the need for less equipment for both the conversion and for the purification of the products obtained.

In process step (a) of the present invention, the propylene oxide is contacted with carbon dioxide in the presence of a homogeneous phosphorus containing catalyst.

The carbon dioxide can be either pure carbon dioxide or carbon dioxide containing further compounds. Carbon dioxide which is especially suitable for use in the present invention is carbon dioxide which has been separated off in subsequent steps of the present process. Carbon dioxide can either be separated off directly after the propylene oxide has reacted with carbon dioxide or at a later stage.

Carbon dioxide is produced in the reaction of the propylene carbonate with water. Therefore, it is especially attractive to separate carbon dioxide at a later stage if water is added in step (c). The carbon dioxide separated in such subsequent process steps can be recycled to step (a) either as such or after having been purified. The extent to which the carbon dioxide is purified depends on the nature and the amounts of contaminants present in the carbon dioxide. These again depend on the exact reaction conditions and purification steps of the process.

The propylene oxide is reacted with carbon dioxide at suitable operating conditions. Such process conditions will generally comprise a temperature of from 50° C. to 200° C., more specifically 100° C. to 150° C., and a pressure of at least $5 \times 10^5$ N/m$^2$, more specifically a pressure of from 5 to $100 \times 10^5$ N/m$^2$, most specifically of from 10 to $30 \times 10^5$ N/m$^2$.

Phosphorus will usually not be present in its elemental form in the catalyst. Phosphorus containing compounds which are suitable catalysts are phosphonium compounds. The catalyst preferably is a homogeneous phosphonium catalyst, more specifically a phosphonium halide catalyst. It was found especially advantageous to employ a tetraalkylphosphonium halide catalyst, more specifically a tributylmethyl phosphonium iodide.

The phosphorus containing catalyst can be either added as such or can be formed in-situ.

The phosphorus containing catalyst may be added to the reactor as a solution of the catalyst in an inert solvent such as in a cyclic carbonate. The catalyst may be added either to the propylene oxide or to the carbon dioxide or to the mixture of both. Preferably, the catalyst solution is added to the mixture of propylene oxide and carbon dioxide.

The reaction mixture obtained in step (a) may be used without further purification in the manufacture of 1,2-propanediol. However, some purification of the reaction mixture may be carried out. A purification which may be advantageous is the removal of at least part of the carbon dioxide from the reaction mixture obtained in step (a) before subjecting the remainder of the reaction mixture to step (c). Such purification can substantially reduce the volume of the reaction mixture to be subjected to step (c). Additional or other purifications can also be carried out as long as the majority of the homogeneous phosphorus containing catalyst remains in the reaction mixture subjected to step (c). Advantageous purification steps depend on the actual process conditions and will be obvious to someone skilled in the art. An example would be the separation of unreacted propylene oxide if the conversion levels are very low.

Water and/or an alcohol may be added to the reaction product containing propylene carbonate and phosphorus containing catalyst. The alcohol used may comprise one or two alcohol groups. Preferably, the alcohol is non-aromatic and is chosen from the group consisting of $C_1$–$C_5$ alkyl alcohols. Preferably, the alcohol is methanol and/or ethanol. Most preferably, the alcohol is methanol.

Either solely water or solely alcohol is preferably added to the reaction product containing propylene carbonate and phosphorus containing catalyst. It is preferred to add water only.

It is especially advantageous if the heterogeneous catalyst compounds catalyze both the hydrolysis reaction if water is added and the transesterification reaction if alcohol is added. Examples of such catalysts comprise solid inorganic compounds such as alumina, silica-alumina, alumina carrying a copper compound, silica-alumina carrying a copper compound, silica-magnesia, aluminosilicate, gallium silicate, zeolites, metal-exchanged zeolites, ammonium-exchanged zeolites, zinc on a support, lanthanum on a support, a mixture of aluminium and magnesium (hydr)oxide and ion-exchange resins.

Preferably, the heterogeneous catalyst employed in step (c) is chosen from the group consisting of a mixture of aluminium and magnesium hydroxide and/or magnesium oxide, zinc on a support, lanthanum on a support and alumina. These catalysts will be described hereinafter in more detail.

The mixture of aluminium and magnesium hydroxide and/or magnesium oxide preferably has a magnesium to aluminium molar ratio in the range of from 3 to 50, more preferably of from 4 to 20. In the preparation of the catalyst, generally, a so-called mixed magnesium/aluminium hydroxide is formed. However, under working conditions mixed magnesium/aluminium oxides may be present. Reference to a mixture of aluminium and magnesium hydroxide and/or magnesium oxide covers both mixtures of aluminium and magnesium hydroxide and mixtures of aluminium and magnesium oxide and a combination of both mixtures. These mixtures were found to give the highest activity at a molar ratio of more that 3, preferably more than 4. A preferred range was found to be of from 4 to 20, more specifically of from 5 to 15, most specifically of from 5 to 10. Preferred catalysts are described in PCT patent application PCT/EP02/12640, which is hereby incorporated by reference.

In another preferred embodiment of the present invention, the catalyst comprises a lanthanum compound on a support. A preferred catalyst comprises at least 7% wt of lanthanum supported on a support. The lanthanum compound preferably is $La_2O_3$ or a precursor thereof. Under reaction conditions this lanthanum compound may be temporarily and/or reversibly converted due to the reaction conditions into lanthanum hydroxide ($La(OH)_3$), lanthanumoxyhydroxide ($LaO(OH)$) and/or corresponding alcoholate species such as ($La(OR)_3$ or $LaO(OR)$).

Any suitable support may be used for the lanthanum containing catalyst. The support preferably is substantially inert under the reaction conditions and is provided with sufficient mechanical strength. Potential supports comprise clay minerals, inorganic supports such as $Al_2O_3$, $SiO_2$, $MgO$, $TiO_2$, $ZrO_2$, $ZnO$ and mixtures thereof. Other examples are a kaolinite, a hallosyte, a chrysotile, a montmorillonite, a beidellite, a hectorite, a sauconite, a muscovite, a phlogopite, a biotite, a hydrotalcite and talc. Particularly preferred are the inorganic supports selected from the group consisting of $Al_2O_3$, $SiO_2$, $MgO$, $TiO_2$, $ZrO_2$, $ZnO$ and mixtures thereof.

The lanthanum containing catalyst comprises, preferably, in the range of from 7 wt % to 40 wt % of lanthanum based on total amount of catalyst. The lanthanum containing catalyst may be produced using any suitable method. A preferred method comprises impregnating a support with a lanthanum containing salt, and subsequently drying and calcining the impregnated support. After impregnation the impregnated support can be dried and subsequently calcined. Calcination is generally carried out at a calcination temperature from between 120° C. to 700° C. The catalyst activity can be increased even further if the catalyst is calcined at a temperature in the range of from 350° C. to 600° C. Preferred catalysts are described in PCT patent application PCT/EP02/12638, herein incorporated by reference.

A further catalyst which is especially suitable for use in step (c) of the present invention is a zinc supported catalyst. The support preferably is selected from the group consisting of $Al_2O_3$, $SiO_2$, $MgO$, $TiO_2$, $ZrO_2$, $Cr_2O_3$, carbon and mixtures thereof. The zinc supported catalyst can be prepared by impregnation of silica, alumina or mixtures of aluminium and magnesium (hydr)oxide with a zinc nitrate solution. Preferably, the zinc supported catalysts comprise at least 15% wt of zinc on a support having a surface area of at least 20 $m^2/g$, more preferably at least 40 $m^2/g$. Preferred catalysts are described in the patent applications claiming priority of European patent application 02256347.2, herein incorporated by reference.

A further catalyst which is preferably used is a catalyst consisting of alumina. Preferably, the alumina is gamma-alumina. Surprisingly, it was found that the alumina catalyst is especially preferred if water is added in step (c), more specifically if only water is added in step (c). Carbon dioxide is released when the propylene carbonate reacts with water and carbon dioxide is well known to cause problems if present with a basic or amphoteric catalyst. Therefore, the constant good performance of the alumina catalyst is unexpected. It was observed that the activity and selectivity of the alumina catalyst remained high even if a substantial amount of carbon dioxide was present such as a carbon dioxide partial pressure of from 5 to $50 \times 10^5$ $N/m^2$, more specifically of from 7 to $40 \times 10^5$ $N/m^2$, most specifically of from 10 to $30 \times 10^5$ $N/m^2$.

If solely water is added to the reaction product containing the propylene carbonate, the process is preferably carried out at a temperature of from 50° C. to 300° C., preferably of from 80° C. to 250° C., more specifically of from 100° C. to 200° C. The pressure can vary widely, and preferably is at most $50 \times 10^5$ $N/m^2$, more specifically at most $20 \times 10^5$ $N/m^2$.

If solely alcohol, more specifically methanol, is added to the reaction product containing the propylene carbonate, the process is preferably carried out at a temperature of from 50° C. to 300° C., more preferably of from 100° C. to 200° C. The pressure preferably is of from 1 to $100 \times 10^5$ $N/m^2$, preferably of from 5 to $60 \times 10^5$ $N/m^2$, more specifically of from 20 to $40 \times 10^5$ $N/m^2$.

The 1,2-propanediol may be separated from the reaction mixture obtained in step (c) in any way known in the art. A further option is to combine steps (c) and (d) by using a catalytic distillation.

A preferred separation comprises one or more distillations of the reaction mixture. One or more of the fractions separated will have a high content of 1,2-propanediol. 1,2-Propanediol obtained by distillation will usually be sufficiently pure to use as such. If required, small amounts of by-products can be removed separately. A well known by-product in the manufacture of 1,2-propanediol is dipropylene glycol. The latter can be removed relatively easily by distillation.

If an alcohol is added in step (c), a dialkyl-carbonate will be present in the reaction product of step (c). In such process in which solely alcohol is added in step (c), the process preferably further comprises separating the dialkylcarbonate from the reaction product in step (d). The dialkylcarbonate can be separated off in any way known to be suitable to someone skilled in the art. Preferably, the dialkylcarbonate is separated in the distillation step(s) by which the 1,2-propanediol is separated off.

The phosphorus containing catalyst which is present in the crude reaction product of step (c), can be separated off from the reaction mixture obtained in step (c) and/or step (d), at least part of which catalyst can be recycled for use in step (a). The phosphorus containing catalyst can be recycled in combination with further compounds either added to or formed in the process according to the present invention. Preferably, the catalyst will be recycled while being dissolved in 1,2-propanediol.

Surprisingly, it was found that the presence of a solvent can be advantageous in the process according to the present invention. A protic solvent was found to reduce decomposition of the phosphorus containing catalyst. 1,2-Propanediol was found to be an especially advantageous solvent. The solvent is preferably present during the whole process such as in the conversion steps (a) and/or (c) and separation steps (b) and/or (d). However, water and/or alcohol is present in steps (c) and (d) while additionally 1,2-propanediol is either being formed or is present in these steps. Therefore, it generally suffices to add protic solvent, preferably 1,2-propanediol, to step (a). The solvent is then present in the subsequent steps. Most preferably, the protic solvent is combined with the phosphorus containing catalyst before being added to step (a).

The present invention is further illustrated by the following examples. These non-limiting examples are given for further illustration of the invention.

EXAMPLE 1

A mixture of water and propylene carbonate was contacted at 150° C. and a carbon dioxide partial pressure of $25 \times 10^5$ N/m$^2$ and a flow of carbon dioxide of 0.1 Nl/hour at a weight hourly space velocity of 0.13 g feed/g catalyst/hour with a catalyst consisting of a mixture of magnesium and aluminium hydroxide having a molar ratio of 5 to 1. Further details both of the feed and of the product obtained are given in Table 1. The phosphonium catalyst was tributyl-methyl-phosphonium iodide.

From Table 1, it is clear that a similar conversion was obtained with feed containing phosphonium catalyst and feed not containing phosphonium catalyst. The feed having a lower water to propylene carbonate molar ratio surprisingly gave a similar conversion even while containing the phosphonium iodide catalyst.

Tributylphosphine oxide and methyldibutyl phosphine oxide are formed in the degradation of tributyl-methyl-phosphonium iodide. The amount of tributylphosphine oxide was measured in the feed before contact with the magnesium and aluminium hydroxide catalyst and in the product after contact with the magnesium and aluminium hydroxide catalyst. Similar amounts were found. From this can be concluded that the heterogeneous catalyst does not degrade the homogeneous, phosphorus containing catalyst.

EXAMPLE 2

An experiment was carried out which was similar to Example 1 but in which a higher weight hourly space velocity was applied.

A mixture of water and propylene carbonate was contacted at 140° C. and a nitrogen pressure of $25 \times 10^5$ N/m$^2$ at a weight hourly space velocity of 15 gram feed/gram catalyst/hour at a water to propylene carbonate molar ratio of 0.36 with a catalyst consisting of a mixture of magnesium and aluminium hydroxide having a molar ratio of 5 to 1. Further details both of the feed and of the product obtained are given in Table 2. The phosphonium catalyst was tributyl-methyl-phosphonium iodide. The feed did not contain 1,2-propanediol.

The examples demonstrate the surprising finding that the homogeneous phosphorus containing catalyst used for converting propylene oxide with carbon dioxide into propylene carbonate is not detrimental for the activity of an active heterogeneous catalyst used in converting the propylene carbonate into 1,2-propanediol. This was observed most conspicuously for phosphonium halide catalysts. No deactivation of the heterogeneous catalyst was seen in processes operated for as long as 1000 hours or more. Equally surprising was the fact that no degradation of the homogeneous phosphorus containing catalyst was observed upon contact with the heterogeneous catalyst.

TABLE 1

| | Feed | | | | | Product |
|---|---|---|---|---|---|---|
| Time on stream (hours) | 1,2-propanediol (mmol/h) | propylene carbonate (mmol/h) | water (mmol/h) | molar ratio of water to propylene carbonate | phosphonium catalyst (mmol/h) | Conversion of propylene carbonate (mole %) |
| 100 | 4.1 | 4.1 | 12.2 | 3 | 0.21 | 98 |
| 500 | 4.3 | 4.3 | 13.0 | 3 | 0.00 | 96 |
| 650 | 4.3 | 4.3 | 8.7 | 2 | 0.23 | 96 |

TABLE 2

| | Feed | | | | Product |
|---|---|---|---|---|---|
| Time on stream (hours) | propylene carbonate (mmol/h) | water (mmol/h) | molar ratio of water to propylene carbonate | phosphonium catalyst (mmol/h) | Conversion of propylene carbonate (mole %) |
| 110 | 278 | 101 | 0.36 | 0.88 | 13 |
| 200 | 272 | 99 | 0.36 | 0.00 | 11 |
| 890 | 276 | 100 | 0.36 | 0.00 | 12 |

We claim:

1. A process for the preparation of 1,2-propanediol from propylene oxide, which process comprises:

(a) contacting propylene oxide with carbon dioxide in the presence of a homogeneous phosphorus containing catalyst and 1,2-propanediol to obtain propylene carbonate;

(b) optionally removing at least part of the carbon dioxide;

(c) adding water and/or an alcohol-to the reaction product containing propylene carbonate and phosphorus containing catalyst and contacting the mixture with a heterogeneous catalyst to obtain 1,2-propanediol in combination with dimethylcarbonate and/or carbon dioxide; and, (d) separating 1,2-propanediol from the reaction product obtained.

2. The process of claim 1, in which the homogeneous phosphorus containing catalyst is a tetraalkylphosphonium halide catalyst.

3. The process of claim 1, in which the heterogeneous catalyst employed in step (c) is chosen from the group consisting of a mixture of aluminium and magnesium hydroxide and/or magnesium oxide, zinc on a support, lanthanum on a support and alumina.

4. The process of claim 3, in which the heterogeneous catalyst comprises a mixture of aluminium and magnesium hydroxide and/or magnesium oxide having a magnesium to aluminium molar ratio in the range of from 4 to 20.

5. The process of claim 1, in which process step (d) comprises distillation of the reaction product of step (c).

6. The process of claim 1, in which process solely alcohol is added in step (c) and which process further comprises separating the dialkylcarbonate from the reaction product in step (d).

7. The process of claim 6, in which the alcohol is methanol and in which the dialkylcarbonate is dimethylcarbonate.

8. The process of claim 1, in which process solely water is added in step (c) whereby 1,2-propanediol is obtained in combination with carbon dioxide.

9. The process of claim 1, in which carbon dioxide is not removed in step (b).

10. The process of claim 1, in which process the homogenous phosphorus containing catalyst is separated off from the reaction mixture obtained in step (c) and/or (d), at least part of which catalyst is recycled for use in step (a).

* * * * *